(12) United States Patent
Groth

(10) Patent No.: US 7,134,550 B2
(45) Date of Patent: Nov. 14, 2006

(54) NEEDLE MAGAZINE

(75) Inventor: Lars Mørch Groth, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 532 days.

(21) Appl. No.: 09/921,429

(22) Filed: Aug. 2, 2001

(65) Prior Publication Data

US 2002/0020647 A1 Feb. 21, 2002

Related U.S. Application Data

(60) Provisional application No. 60/225,228, filed on Aug. 14, 2000.

(30) Foreign Application Priority Data

Aug. 3, 2000 (DK) ................................ 2000 01167

(51) Int. Cl.
*B65D 83/10* (2006.01)
*B65D 85/28* (2006.01)
(52) U.S. Cl. ...................................... 206/366; 206/380
(58) Field of Classification Search ........ 206/363–366, 206/380, 382, 383, 370, 460; 220/908; 422/933; 604/110, 192, 240–242; 222/169, 170, 167; 221/26, 125, 310
See application file for complete search history.

(56) References Cited

U.S. PATENT DOCUMENTS

| | | | |
|---|---|---|---|
| 2,573,311 A | 10/1951 | Cupler, II | |
| 2,771,182 A * | 11/1956 | Messmer | 206/382 |
| 4,203,518 A * | 5/1980 | Current | 206/380 |
| 4,383,615 A * | 5/1983 | Aquino | 206/366 |
| 4,449,630 A | 5/1984 | Filhol | |
| 4,524,891 A | 6/1985 | Silva | |
| 4,586,614 A | 5/1986 | Ger | |
| 5,150,788 A | 9/1992 | Weissman | |
| 5,347,078 A * | 9/1994 | Eckels | 206/365 |
| 5,451,213 A * | 9/1995 | Teicher et al. | 604/192 |
| 5,595,296 A | 1/1997 | Wood | |
| 5,799,788 A | 9/1998 | Webb | |
| 5,873,462 A | 2/1999 | Nguyen et al. | |
| 5,971,966 A | 10/1999 | Lav | |
| 5,975,295 A * | 11/1999 | Diamond | 206/366 |

FOREIGN PATENT DOCUMENTS

| | | |
|---|---|---|
| FR | 2661159 | 10/1991 |
| WO | WO 98/29322 | 7/1998 |

\* cited by examiner

*Primary Examiner*—Mickey Yu
*Assistant Examiner*—J. Gregory Pickett
(74) *Attorney, Agent, or Firm*—Marc A. Began; Reza Green; Richard W. Bork

(57) ABSTRACT

A needle magazine for storing a plurality of needle assemblies and for selectively dispensing said needle assemblies there from. The needle magazine comprises a cylinder-shaped base member with an upper surface and a bottom surface. These two surfaces are parallel to each other and connected by a cylinder-shaped surface. The base-member is provided with a number of compartments each having the form of a sector of a circle. Each compartment contains a needle assembly positioned in a horizontal position. The base member is at least partly covered by a cover having a first part parallel with the upper surface and a second part parallel with the cylinder-shaped surface of the base member, and which second part is provided with an opening through which access to each compartment can be gained radial of the axis of rotation of the cover.

4 Claims, 3 Drawing Sheets

NEEDLE MAGAZINE

This application claims the benefit of provisional application 60/225,228 filed on Aug. 14, 2000.

The invention relates to a needle magazine for storing and dispensing a number of needle assemblies.

Medical injection devices are used to deliver selected doses of medication to patients. Some medication, such as insulin is self-administered. The typical diabetes patient will require injections of insulin several times during the course of the day. In order to prevent infections it is recommended to use a sterile needle assembly for each new injection. Needle assemblies are often delivered in magazines where each magazine contains only one needle assembly in a sterile compartment. Such a magazine is described in U.S. Pat. No. 5,971,966. Using a needle assembly of this kind requires the patient to open the magazine and to fasten the needle assembly onto the injection device prior to each injection. The storage of sterile needle assemblies of this type and the final disposal of used needle assemblies present a problem, since new sterile needle assemblies are often carried loosely in purses or briefcases, and used needle assemblies are often disposed of unsafely.

To overcome these problems a needle magazine for storage and dispensing a plurality of needle assemblies has been developed. This prior art magazine is shown in U.S. Pat. No. 5,873,462 and is made from a cylinder-shaped base-member having a plurality of compartments each compartment containing a needle assembly. A cover is rotatably mounted on top of the base-member. When aligning a slot provided in the cover with the interior of the compartment, the user can access the compartment. The needle assembly is connected to the injection device by a thread connection. A typical injection device has a thread provided on the tip, which thread is fitted over the interior thread of the needle assembly, thus when rotating either the magazine or the injection device the needle assembly is connected to the injection device. When the used needle assembly is to be placed in the magazine after use the user has to conduct the same procedure again.

The handling of the known needle magazine is very cumbersome since the height of the magazine makes it difficult to hold in one hand. The magazine therefore has to be placed on a flat surface e.g. a table, prior to loading a needle assembly on to an injection device. The users physical control over the needle magazine is somewhat limited, when the magazine is located on a table. The pitch of the thread connection between the injection device and the needle assembly are typically made such that the injection device must be rotated twice i.e. approximately 720 degrees, in order to make the thread connection sufficient fluid tight.

It is an object of the present invention to provide a needle magazine, which does not posses the drawbacks of the prior art needle magazines, and where it is possible to utilize the needle magazine as the lever of a wrench when connecting the injection device with the needle assembly, thereby rendering it considerable easier to change the needle assembly. It is also an objective to provide a needle magazine where the number of times the injection device has to be rotated, in order to fit the needle assembly onto the injection device, is minimized.

This is obtained by a needle magazine for storing a plurality of needle assemblies and for selectively dispensing said needle assemblies there from, comprising:

a cylinder-shaped base member having an upper surface and a bottom surface and a cylindrical surface there between, which base member includes a number of compartments, each compartment containing one of said needle assemblies, and a cover rotatably mounted on said base member for rotation relative to said base member, said cover having a slot through which access to a needle assembly located in one of said compartments can be provided, which needle magazine according to the invention is characterized in that each compartment has at least partly the form of a sector of a circle, each sector extending radially of the axis of rotation of said cover, said cover has a first part which is substantial parallel with said upper surface and a second part which is substantial parallel with said cylindrical surface, which second part at least partly covers the cylindrical surface of said cylinder-shaped base member, and that said slot in said cover is at least partly provided in said second part, such that access to said compartment can be gained radially of the axis of rotation of said rotary member An ordinary needle assembly for an injection device e.g. a Novofine needle assembly from Novo Nordisk A/S, has a length approximately twice the diameter of the hub carrying the thread. When storing each needle assembly in the magazine in the horizontal direction instead of in the vertical direction it is possible to cut the height of the magazine from encompassing the length of the needle assembly down to only encompassing the diameter of the needle assembly, which is approximately half the height. At the same time, the same number of needles can be stored in a magazine having the same diameter as the known magazine, thus the centre-area of the magazine is now being utilized for storage space.

When the height of the needle magazine is diminished it is possible to fit the magazine in the palm of a hand. When doing so the magazine can be rotated as a wrench with one hand, while the injection device can be rotated with the other hand, in this way each part only has to be rotated once i.e. 360 degrees, in order to connect the needle assembly with the injection device.

When the user grasps the magazine in the palm of a hand and rotates it relatively to the injection device onto which the needle assembly is to be connected, most of the force used is applied displaced from the axis of rotation of the magazine. The magazine is in that way used as the lever of a wrench, which makes it easier for people with limited physical strength or motoricity to connect the needle assembly to the injection device.

When each compartment has means locking each needle assembly against rotation, it is ensured that the needle assembly is rotated together with the needle magazine whenever this is rotated relatively to the injection device. A simple way of rotational connecting the needle assembly with the needle magazine is by force fitting each needle assembly into each compartment. Yet another way of locking the needle hub rotational to the base member could be by providing the needle hub with longitudinal tracks or ribs fitting into similar tracks or ribs located on the interior surface of the compartment.

When each compartment has means preventing reuse of used needle assemblies, it is ensured that the user cannot reuse a used needle assembly and thereby unwillingly be infected. One way of hindering reuse of the used needles after deployment in the needle magazine is by providing each compartment with a number of flexible arms located on the interior surface of each compartment, which arms has a build in resiliency moving the arms into a position perpendicular to the interior surface of each compartment.

When the arms are bended forward and wedged between the outside diameter of the needle hub or the ring carried on the needle hub and the compartment when a used needle assembly is deployed in the compartment, it is ensured that the used needle assemblies stays securely locked in the compartment.

When the needle magazine has means preventing the cover from rotating in one rotational direction relatively to the base member, it is ensured that the opening in the cover can only be moved in one direction, which direction will be the direction revealing fresh and sterile needle assemblies. A simple way of utilizing these means would be to provide the needle magazine with a plurality of ratchet teeth provided on the base member that interacts with one or more ratchet teeth provided the cover.

When the cover and the base member has means preventing the cover from rotating more than 360 degrees relatively to said base member, it is ensured that once all the needle assemblies of a needle magazine is used the opening in the cover can not be moved further. One way of ensuring this is by having a first protrusion located on the cover and a second protrusion located on the base member abutting each other when the cover is rotated approximately 360 degrees relatively to the base member.

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

Figure 1:
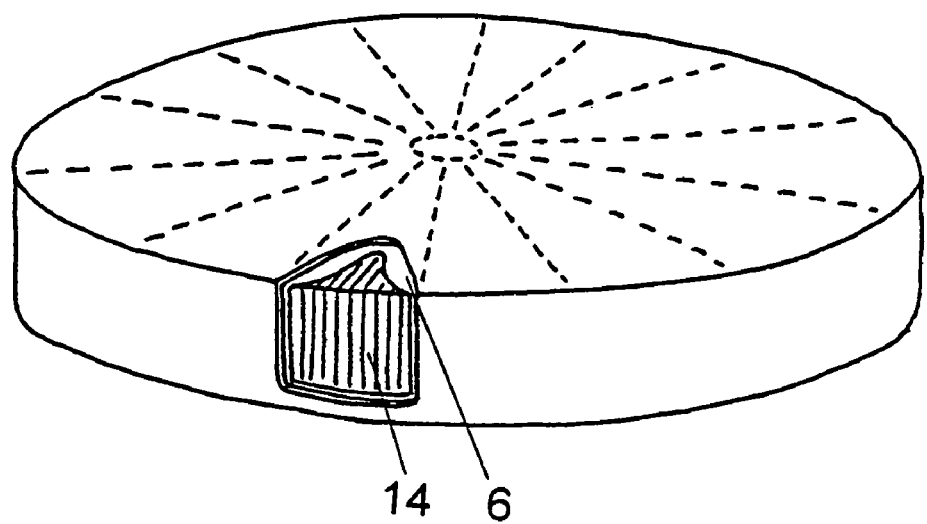
FIG. 1 Shows a perspective view of the needle magazine according to the invention.
Figure 2:
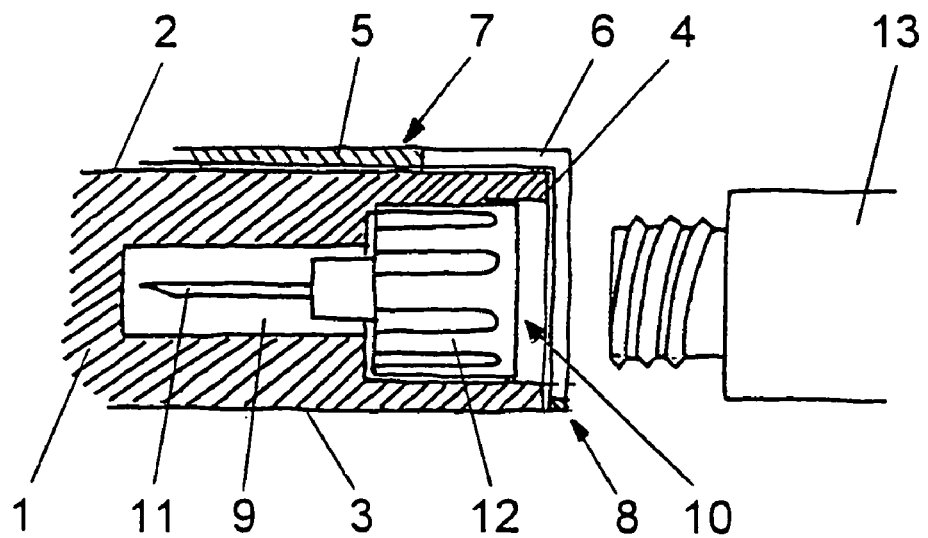
FIG. 2 Shows a sectional side view of the needle magazine according to the invention.

FIGS. 1 and 2 shows the needle magazine according to the invention. The needle magazine comprises a cylinder-shaped base member 1 with an upper surface 2 and a bottom surface 3. These two surfaces 2, 3 are parallel to each other and connected by a cylinder-shaped surface 4. The upper surface 2 is covered by a cover 5, which cover 5 is connected to the circular base-member 1 either at the centre of the circular base member 1 or at surface 4. The base-member 1 and the cover 5 can rotate relative to each other, and both parts can be provided with a number of not shown finger grips making it easier for the user to perform the rotational movement.

The base member 1 is provided with a number of compartments 9, each compartment 9 containing a needle assembly 10. Each needle assembly 10 comprises a needle cannula 11 and a needle hub 12. The needle cannula 11 has a distal end for piercing the skin of the user and a proximal end for piercing the elastomeric seal of a not shown cartridge containing the medicine to be expelled. The needle hub 12 is connected to the needle cannula 11, and carries means for connecting the needle hub 12 with the injection device 13.

The base member 1 is circular and each compartment 9 has, at least partly, the form of a sector of a circle. Each sector or compartment 9 extends radially of the axis of rotation of the cover 5.

The means connecting the injection device 13 and the hub 12 can, as shown in FIG. 2, be an ordinary thread connection. When connecting the needle assembly 10 and the injection device, the tip of injection device 13 is pushed into the needle hub 12 and the injection device 13 is rotated relatively to the needle magazine. Each needle assembly 10 is located one by one in the compartments 9 in a way preventing the needle assemblies 10 from rotating whenever the injection device 13 is rotated, the needle assemblies 10 can e.g. be initially force fitted into the compartments 9, or the needle assemblies 10 can be provided with longitudinal tracks or ribs fitting into similar tracks or ribs located on the interior surface of the compartment 9, thereby locking the needle hubs 12 rotational to the base member 1. Each compartment 9 is sealed by a sterility membrane 14, which e.g. can be a pealable label 14. In this way the interior of each compartment 9 can be kept sterile, while access can be gained simply by removing the pealable label 14.

The cover 5, which preferably is made from a suitable polymeric material, has a first part 7 being substantially parallel with the upper surface 2 of the base member 1, and a second part 8 being substantially parallel with the cylindrical surface 4 of the base member 1 of the rotary member 5. The cover 5 can be fully or partly transparent allowing the user to visually inspect the compartments 9. The cover 5 is provided with an opening 6 through which access to each compartment 9 can be gained. The opening 6 is located in the part of the cover 5, which is parallel to the cylindrical surface 4 of the base member 1 since access to each compartment 9 is provided from the radial side of the needle magazine. A part of the opening 6 is however also located in the part of the cover 5, which is parallel to the upper surface 2 of the base member 1. In this way it is possible for the user to reach the flap on the pealable label 14.

The compartments 9 are accessed by the user from the radial side of the needle magazine i.e. from the cylindrical surface 4 of the base member 1. The cover 5 is rotated such that the opening 6 is aligned with one of the compartments 9. Means clicking the cover 5 into the aligned position can be provided. When the opening 6 is aligned with one of the compartments 9 containing a sterile needle assembly 10, the pealable label 14 can be removed, and the tip of injection device 13 can be inserted through the opening 6. The injection device 13 and the needle magazine is then rotated relatively to each other for connecting the thread of the needle hub 12 onto the thread located on the tip of the injection device 13. When pulling the injection device 13 away from the needle magazine in the radial direction the injection device 13 now carrying the needle assembly 10 is ready to use. After use the needle assembly 10 is brought back in the same compartment 9 by reversing the movements described.

Figure 3:
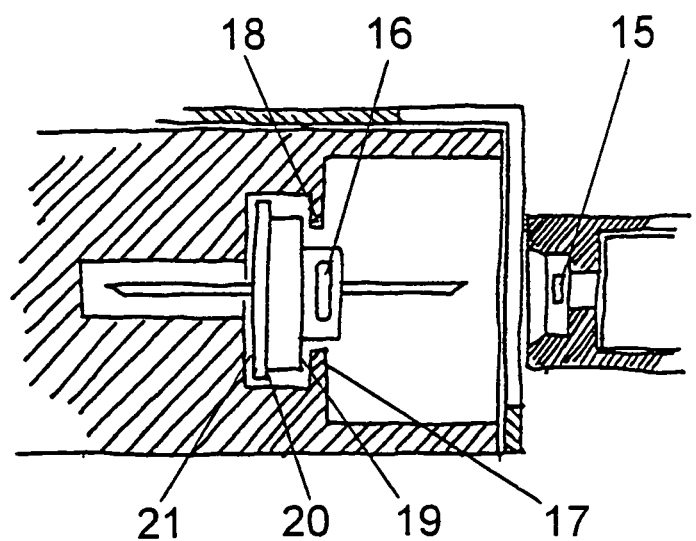
FIG. 3 Shows a sectional view of an embodiment of the invention, with the needle assembly in the detached position.
Figure 4:
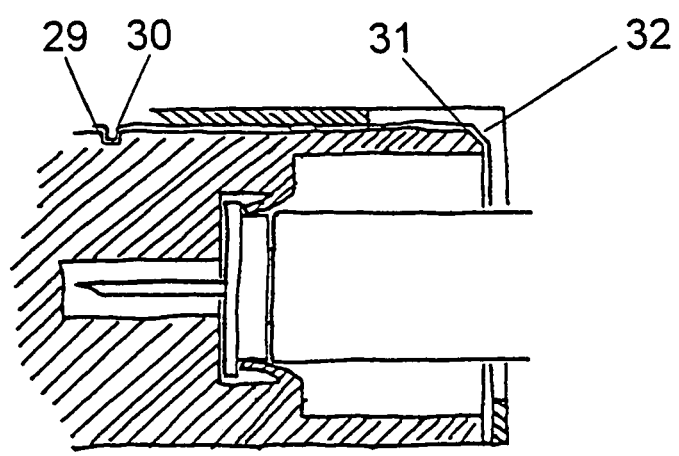
FIG. 4 Shows a sectional view of an embodiment of the invention, with the needle assembly in the attached position.

Means locking the needle assembly 10 in the base member 1 once the used needle assembly 10 is returned to the base member 1 can be provided. An example of such means is shown in FIGS. 3 and 4.

In these figures the connection between the injection device 13 and the needle assembly 10 is shown as a bayonet coupling, but the principles described could off cause be utilized on the previous described thread connection if so wanted.

The bayonet coupling comprises a protrusion 15 on the tip of the injection device 13, which protrusion, when the needle assembly 10 is carried on the injection device 13 is located on the distal side of a protrusion 16 provided on the needle hub 12. The protrusion 16 on the needle hub 12 is usable longer than the protrusion 15 on the injection device 13, and can be provided at an oblique angle, such that the needle hub 12 will be pulled tight against the injection device 13 when the injection device 13 is rotated relatively to the needle magazine. Usually the needle hub 12 is provided with two or more such protrusions 16 located with an angular displacement.

Each compartment 9 in the base member 1 of the needle magazine is on the interior surface provided with a number of flexible arms 17, 18. These arms are originated in a position perpendicular to the interior surface, and has a build in resiliency, which at all times will try to raise the arms into their original perpendicular position. At the same time the needle hub 12 is provided with a first shoulder 19 and a second shoulder 20, both shoulders 19, 20 encircling the needle hub 12. The needle assembly 10 is initially located in the compartment 9 with the flexible arms 17, 18 being perpendicular to the interior surface of the compartment 9. In this position the arms 17, 18 abuts the first shoulder 19. It is to be understood that the arms 17, 18 can be provided as a random number of individual arms 17, 18 located along the inside surface of each compartment. The arms 17, 18 can be provided as tongues located side by side on all 360 degrees of the interior surface of the compartments 9, or they can be located with an angular displacement along the inside surface of the compartments, or the arms 17, 18 can be provided as one circular skirt provided on the inside surface of the compartments 9.

When connecting the needle hub 12 to the injection device 13, the tip of the injection device 13 is pushed into the needle hub 12 and rotated a little relatively to the needle magazine in order to secure the bayonet coupling. When pulling the injection device 13 away from the needle magazine in the radial direction the shoulders 19, 20 on the needle hub 12 bends the flexible arms 17, 18 backwards allowing the needle hub 12 to pass.

A slot, into which the protrusion 15 fits, can replace the protrusion 16. The needle hub 12 and the injection device 13 is then simply connected by pushing the tip of the injection device 13 into the interior of the needle hub 12 until the protrusion 15 clicks into the slot.

To clarify the various directions used, backwards describes the direction away from the centre of the needle magazine, and forward describes the opposite direction i.e. the direction pointing towards the centre of the needle magazine.

After use the needle assembly is relocated in the needle magazine by pushing the injection device 13 carrying the needle assembly 10 forward through the opening 6 in the cover 5 and into the compartment 9 in the base member 1. By doing so the distal surface 21 of the needle hub 12 bends the flexible arms 17, 18 forward. Once the distal surface 21 has passed the flexible arms 17, 18, the build in resiliency of the arms 17, 18 bends them backwards, they are however prevented from bending all the way backwards and into the perpendicular position due to the size of the diameter of the needle hub 12 between the first shoulder 19 and the second shoulder 20. The flexible arms 17, 18 are in this position pointing forward and abutting both the second shoulder 20 and the needle hub 12. With the needle hub 12 now wedged between the flexible arms 17, 18, as shown in FIG. 4, it is impossible to pull the needle hub 12 backwards further out of the base member 1.

In order to prevent reuse of the needle assemblies 10 the needle magazine can be equipped with means for preventing the cover 5 from rotating in one direction relative to the base member 1. These means could be a plurality of ratchet teeth 29 provided on the base member 1 that interacts with one or more ratchet teeth 30 provided on the cover 5. The ratchet teeth 29, 30 preferably have a steep side and a ramp shaped side thereby only allowing rotation in one direction. Similar means can be provided for indexing the openings 6 in the cover 5 in alignment with each compartment 9.

The needle magazine can have additional means for preventing the cover 6 from rotating more than 360 degrees relative to the base member 1. This means could be a first not shown protrusion located in a circular track 31 on the base member 1 and a second protrusion 32 located on the cover 5, which protrusions abut each other when the cover 5 is rotated approximately 360 degrees relative to the base member 1.

Figure 5:
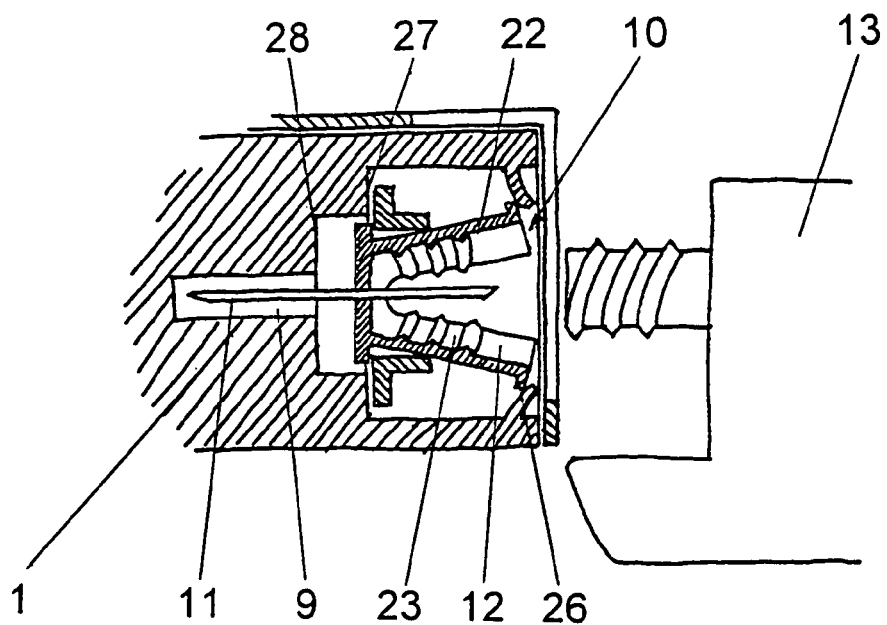
FIG. 5 Shows a sectional view of another embodiment of the invention, with the needle assembly in the detached position.
Figure 6:
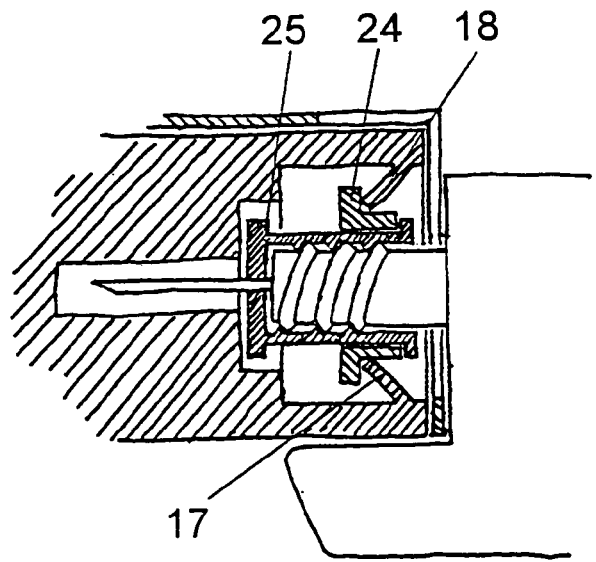
FIG. 6 Shows a sectional view of another embodiment of the invention, with the needle assembly in the attached position.

In order to accommodate those injection devices 13, which, due to their design, cannot be rotated, a click-on, click-off connection has been developed. This connection is shown in FIGS. 5 and 6.

The needle assembly 10 comprises a needle cannula 11 and a needle hub 12. The needle hub 12 is in the longitudinal direction divided into at least two flaps 22, 23 by a number of longitudinal located slots, which are open in the proximal end of the needle hub 12 and extends in a direction from the proximal end of the needle hub 12 towards the distal end of the needle hub 12. The number of slots is preferably two, but could as well be three or four.

A hollow ring 24 is slidable located on the outside diameter of the needle hub 12. The ring 24 can slide freely between a first collar 25 located at the distal end of the needle hub and a second collar 26 located on the proximal end of the needle hub 12.

Each compartment 9 in the base member 1 of the needle magazine is on the interior surface provided with a number of flexible arms 17, 18. The compartment 9 is also provided with a first shoulder 27 and a second shoulder 28, both shoulders 27, 28 being formed as a circular end-wall of the compartment 9. The needle assembly 10 is initially located in the compartment 9 with the flexible arms 17, 18 being bended a little backwards abutting and holding the needle hub 12 inside the compartment. In this position, as shown in FIG. 5, the ring 24 abuts the first shoulder 27.

When the threaded tip of the injection device 13 is pushed into the split-open end of the needle hub 12, the needle hub 12 is pushed further forward while the ring 24 abutting the first shoulder 27 is slided along the needle hub 12, thereby tightening the flaps 22, 23 around the threaded tip of the injection device 13. When the ring 24 abuts the second collar 26 on the needle hub 12, the flaps are fully tightened and the needle assembly 10 attached to the injection device 13 can be pulled away from the needle magazine.

After use the needle assembly is relocated in the needle magazine by pushing the injection device 13 carrying the needle assembly 10 forward through the opening 6 in the cover 5 and into the compartment 9 in the base member 1. By doing so the ring 24 bends the flexible arms 17, 18 forwards. When pulling the injection device 13 backwards away from the needle magazine the arms 17, 18 are however prevented from bending all the way backwards and into the perpendicular position due to the size of the diameter of the ring 24 between the first collar 25 and the second collar 26.

The flexible arms 17, 18 are in this position pointing forward and abutting the ring 24. With the ring 24 and the needle hub 12 now wedged between the flexible arms 17, 18, as shown in FIG. 6, it is impossible to pull the needle hub 12 further backwards out of the base member 1, and further backwards pulling of the injection device will result in the ring being slided along the outside surface of the needle hub until the ring 24 reached the first collar 25, at this point the flaps 22, 23 of the needle hub 12 will be repelled enough for the injection device 13 to disconnect from the needle assembly 10.

Some preferred embodiments have been shown in the foregoing, but it should be stressed that the invention is not limited to these, but may be embodied in other ways within the subject matter defined in the following claims.

The invention claimed is:

1. A tool for attaching a pen needle assembly, which comprises a hub and needle cannula mounted to the hub, to an injection device that has a needle mounting surface disposed thereon, the tool comprising:
   a. a cylindrical storage member having elongated cavities complementaly in size and shape to the pen needle assembly, the cavities arranged radially in the cylindrical member so as to allow the tool to rotate about an axis of rotation that is concentric with the cavity's longitudinal axis;
   b. a rotatable cover mounted on the storage member having a cylindrical wall and having an opening that allows access to one cavity at a time;
   c. a removeably sterility barrier sealing the cavities;
   wherein: the height of the cylindrical member and cover are sized so as to allow a user to grasp the tool in one hand and to rotate the tool in one hand 360 degrees about the axis of rotation while simultaneously allowing the user to rotate the injection device 360 degrees in an other hand, wherein when the tool is grasped in the hand of a user, the majority of rotational force applied to the tool occurs at a distance displaced away from the axis of rotation of the tool, thereby maximizing the rotational force on the pen needle assembly.

2. The tool of claim 1, further comprising a means for preventing rotation of the cover over the same opening more than once.

3. A method of mounting a pen needle assembly, which comprises a hub and needle cannula mounted to the hub, to an injection device that has a needle mounting surface disposed thereon, the method comprising the steps of:
   obtaining a tool that comprises
   a. cylindrical storage member having elongated cavities complementary in size and shape to the pen needle assembly, the cavities arranged radially in the cylindrical member so as to allow the tool to rotate about an axis of rotation that is concentric with the cavity's longitudinal axis;
   b. a rotatable cover mounted on the storage member having a cylindrical wall and having an opening that allows access to one cavity at a time;
   c. a removeably sterility barrier sealing the cavities;
   wherein: the diameter of the cylindrical member and the cover is substantially larger than the height of the cylindrical member and cover, respectively; the height of the cylindrical member and cover are sized so as to allow a user to grasp and rotate the tool in one hand 360 degrees about the axis of rotation while simultaneously allowing the user to rotate the injection device 360 degrees in an other hand, wherein when the tool is grasped in the hand of a user, the majority of rotational force applied to the tool occurs at a distance displaced away from the axis of rotation of the tool, thereby maximizing the rotational force on the pen needle assembly;
   removing the sterility barrier;
   grasping the tool in one hand and the injection device in another;
   rotating the tool 360 degrees;
   rotating the injection device 360 degrees;
   wherein the grasping of the tool occurs at a distance displaced away from the axis of rotation of the tool so as to maximize the rotational force on the pen needle assembly.

4. A needle storage and mounting apparatus for storing a plurality of pen needles and mounting one of the needles onto an injection device, the apparatus comprising:
   a cylindrical body having radial cavities complementary in shape to the pen needles;
   a cylindrical cover having one opening for accessing one cavity at a time, the cover being rotatable so that the opening can be rotated over a cavity;
   a means for preventing the opening in the cover from being rotated over the same opening more than once;
   a means for preventing rotation of the pen needle while the needle is in the cavity;
   and wherein the apparatus has a height and diameter and wherein the diameter is substantially greater than the height so that a user may grasp the apparatus in one hand, exert a rotational force on the apparatus at a two points equidistant from the pen needle thereby maximizing the rotational force on the pen needle and assisting in screwing the pen needle onto the injection device.

* * * * *